(12) United States Patent
Bjellqvist et al.

(10) Patent No.: US 9,341,595 B2
(45) Date of Patent: May 17, 2016

(54) ELECTROPHORESIS GEL ASSEMBLY

(75) Inventors: Bengt Bjellqvist, Stockholm (SE); Elsemarie Bjellqvist, legal representative, Stockholm (SE); Henrik Ostlin, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 813 days.

(21) Appl. No.: 13/521,281

(22) PCT Filed: Jan. 10, 2011

(86) PCT No.: PCT/SE2011/050011
§ 371 (c)(1),
(2), (4) Date: Jan. 18, 2013

(87) PCT Pub. No.: WO2011/084102
PCT Pub. Date: Jul. 14, 2011

(65) Prior Publication Data
US 2013/0168248 A1    Jul. 4, 2013

(30) Foreign Application Priority Data
Jan. 11, 2010    (SE) ..................... 1050010

(51) Int. Cl.
*G01N 27/447*    (2006.01)
(52) U.S. Cl.
CPC .... *G01N 27/44795* (2013.01); *G01N 27/44704* (2013.01)

(58) Field of Classification Search
CPC ............... G01N 27/44795; G01N 27/44704
USPC ........................... 204/459, 548, 610, 644
See application file for complete search history.

(56) References Cited

U.S. PATENT DOCUMENTS

| 5,288,465 | A  | * | 2/1994  | Margolis ................ 204/619 |
| 5,858,187 | A  | * | 1/1999  | Ramsey et al. ........... 204/452 |
| 6,413,402 | B1 |   | 7/2002  | Manusu et al. |
| 2004/0050698 | A1 | | 3/2004 | Eckerskorn et al. |
| 2004/0222097 | A1 | | 11/2004 | Koh et al. |
| 2010/0213065 | A1 | * | 8/2010 | Astrom et al. ............ 204/459 |

OTHER PUBLICATIONS

Swank et al. (J Neurosci. Meth. 158, 2006, pp. 224-233).*
Swank, M., et al., Journal of Neuroscience Methods, 158:224-233 (2006).

* cited by examiner

*Primary Examiner* — Luan Van
*Assistant Examiner* — Steven Rosenwald
(74) *Attorney, Agent, or Firm* — Sutherland Asbill & Brennan LLP

(57) ABSTRACT

An electrophoresis gel assembly comprising a gel slab, at least two sample wells and at least one focusing buffer well arranged between two adjacent sample wells and wherein focusing barriers are arranged between the focusing buffer well and the sample wells. A high conductivity focusing buffer can be applied to the focusing buffer well to obtain a lateral focusing of the sample bands during electrophoresis.

21 Claims, 6 Drawing Sheets

ELECTROPHORESIS GEL ASSEMBLY

CROSS-REFERENCE TO RELATED APPLICATIONS

This application is a filing under 35 U.S.C. 371 of international application number PCT/SE2011/050011, filed Jan. 10, 2011, published on Jul. 14, 2011 as WO 2011/084102, which claims priority to application number 1050010-6 filed in Sweden on Jan. 11, 2010.

TECHNICAL FIELD

The present invention relates generally to separation and analysis of biomolecules and specifically to gel electrophoresis of biomolecules. More particularly the invention relates to a construction and a method for lateral focusing of bands in electrophoresis.

BACKGROUND OF THE INVENTION

Gel electrophoresis is a widely used method for separating biomolecules, such as proteins, peptides, nucleic acids etc. Gel electrophoresis involves the migration of electrically charged molecules in an electric field. A solution containing biomolecules is placed in contact with a supporting gel, an electric field is applied and the molecules are allowed to migrate on or through the electrophoretic gel. Electrophoretic separation of molecules is based on the difference in charge density of the molecules as well as the sieving effect of the porous gel media.

The normal procedure when electrophoresis is done in horizontal or vertical slab gels is to apply a number of samples and run them in parallel sample lanes so that the sample components in each lane separates into a number of bands. There are a number of reasons why the sample lanes should be kept as narrow as possible. One point is that decreased widths of the sample lanes allow a larger number of samples to be run on a gel slab of given size. Another point is that the sensitivity with which the biomolecules can be detected and measured is inversely proportional to the width of the sample lanes. Narrow lanes are also advantageous in situations, where the whole sample lane or parts of the lane after finished electrophoresis need to be transferred and use in connection with a second technique such as Western blotting, 2-D electrophoresis or tryptic digestion followed by MS.

With currently used techniques the width of the sample lanes are mainly determined by the width of the sample application zone. Easy and convenient manual sample application with a micro-pipette require a minimum width of the sample application zones of the order of 2-3 mm, but for best possible sensitivity the width of the sample lanes should be in the order of 0.2-0.5 mm. The combination of narrow sample lanes with the use of thin gels, required for best possible resolution, drastically limit the sample volumes possible to use. To use narrow high sample application cups on a thin horizontal gel is not a solution, unless the samples contain low salt and buffer concentrations. Due to the distortions of the electric field around a sample cup, used in this manner, the biomolecules will spread laterally as they leave the cup and enter the gel. The result is a sample lane much wider than the used application zone.

M W Swank et al (J Neurosci Meth 158 (2006) 224-233) describe slab gels where paper strips saturated with high ionic strength buffer are pressed onto the gel between the sample application zones, to provide an electric field gradient that gives some lateral focusing of the sample lanes. This setup is complex, requires careful manual handling, so there is a need for a more convenient solution.

BRIEF DESCRIPTION OF THE INVENTION

One aspect of the present invention is to provide a parallel electrophoretic separation of at least two samples with lateral focusing of the sample lanes. This is achieved with an electrophoresis gel assembly 1 comprising a gel slab 20, at least two sample wells 3 and at least one focusing buffer well 4 arranged between two adjacent sample wells and wherein focusing barriers 2 are arranged between the buffer well and the sample wells. It is also achieved with a method for electrophoretic separation of biomolecules on a gel assembly as described above.

DEFINITIONS

Figure 1:
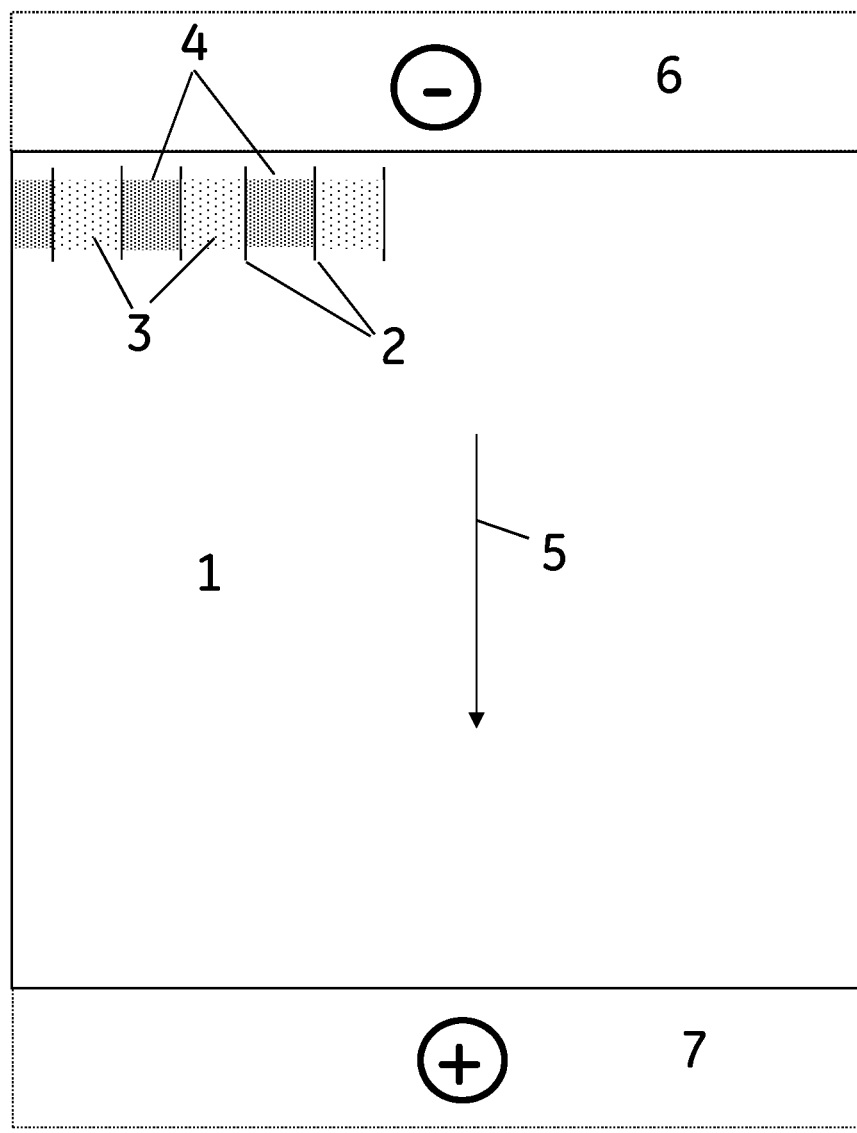
FIG. 1 shows an electrophoresis gel assembly according to one embodiment of the invention.

The term "electrophoresis gel assembly" means herein a gel slab (e.g. a polyacrylamide hydrogel) intended for electrophoretic separation of e.g. biomolecules, complete with any externally applied devices such as sample cups, buffer cups/channels, barriers, supports, cassettes etc. to be used during the electrophoresis.

The term "sample buffer" means herein a buffer in a biomolecule sample to be separated using the electrophoresis gel assembly. Examples of sample buffers can be 1 mM-0.1 M Tris-HCl or Tris-$H_3PO_4$ buffers, optionally with other components such as denaturing agents, dyes, complexing agents etc. present.

The term "gel buffer" means herein the buffer present in the gel slab before electrophoresis, which can typically be added to the monomer solution before casting of the gel slab. Examples of gel buffers can be 1 mM-1 M Tris-HCl, Tris-$H_2SO_4$, Tris-glycine, Tris-HAc or Tris-boric acid buffers. In some cases separate buffers can be present in the stacking gel (at the sample application end of the gel slab) and in the separation gel (the major part of the gel slab), in which case the respective buffers are called "stacking gel buffer" and "separation gel buffer".

The term "electrode buffer" means herein the buffer in contact with the electrodes, such as in electrode compartments or in buffer strips contacting the electrodes. The electrode buffer can provide the contact between the electrodes and the gel slab and act as a reservoir of buffer ions. An example of an electrode buffer can be 0.01-1 M Tris-glycine. In some cases separate buffers in contact with the anode and the cathode can be used. They are then called "anode buffer" and "cathode buffer".

The term "focusing buffer" means herein a buffer of at least 25%, 100%, 200% or 600% higher electrical conductivity than at least one biomolecule sample applied to the gel. The focusing buffer may comprise the same buffering species as a sample buffer, in which case the higher conductivity can be achieved by increasing the concentration of the buffering species, adding a non-buffering salt and/or changing pH. The focusing buffer may also comprise buffering species not present in a sample, in which case the choice of buffering species offers an additional possibility to manipulate the conductivity.

The term "focusing barrier" means herein a thin (e.g. <2 mm thickness) electrically non-conductive diffusion barrier, restricting or preventing lateral transport of ions or electrons between the sample wells and the focusing buffer wells. A focusing barrier can be a standing wall-like structure transverse to the gel plane, manufactured from e.g. plastics, glass or ceramics.

The term "well" means herein an open or closed compartment intended for receiving a liquid. Receiving a liquid may involve at least partial filling with a liquid. The compartment may be defined by a recess in the gel slab, by physical delimitations (cups, barriers, combs, cassette features etc) or simply by a designated area on the gel slab surface. A "sample well" means a well intended to receive a sample and a "focusing buffer well" means a well intended to receive a focusing buffer.

DETAILED DESCRIPTION OF THE INVENTION

Figure 2:
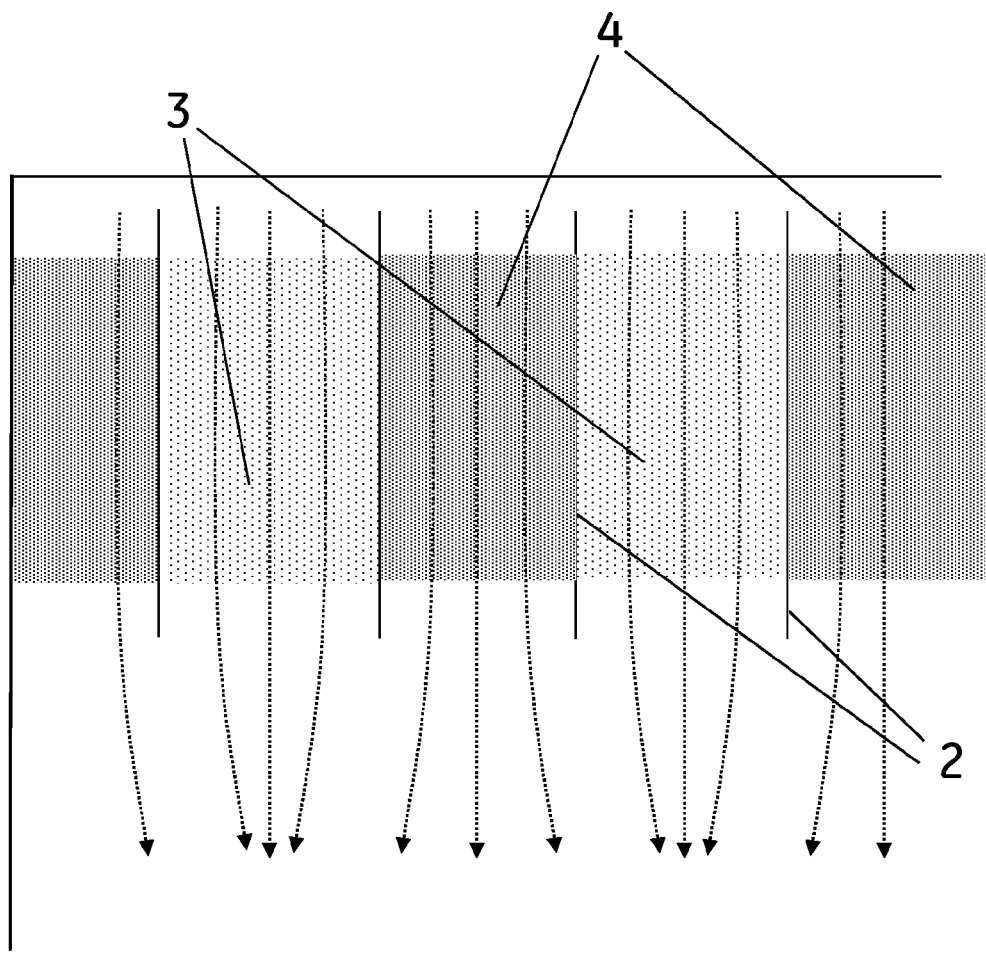
FIG. 2 shows an enlargement of the gel assembly in FIG. 1.

One embodiment of the invention, illustrated by FIGS. 1 and 2, is an electrophoresis gel assembly 1 comprising a gel slab, at least two sample wells 3 and at least one focusing buffer well 4 arranged between two adjacent sample wells and wherein focusing barriers 2 are arranged between the focusing buffer well and the sample wells. Cathode and anode buffers can be supplied from the respective buffer supplies 6,7, which can be buffer tanks or buffer strips/wicks. The gel slab may comprise a large pore stacking gel and a smaller pore separation gel. It may comprise a gel buffer or separate stacking gel and separation gel buffers. A focusing buffer of higher conductivity than the sample buffer can be supplied to the focusing buffer well. An advantage of this is that during electrophoresis, due to the higher current density in the focusing buffer well areas, the electric field between the anode and the cathode will converge laterally towards the sample lanes as indicated in FIG. 2, giving a focusing action on the migrating sample bands. Hence, the bands will be narrower in the lateral direction than in the absence of the focusing buffer, providing possibilities for a) higher sensitivity (the local concentration in the bands is increased) and b) application of a larger number of samples on the gel. The focusing barrier arrangement is suitably compatible with automated sample and buffer application procedures and offers a high degree of convenience also for manual application.

Figure 4:
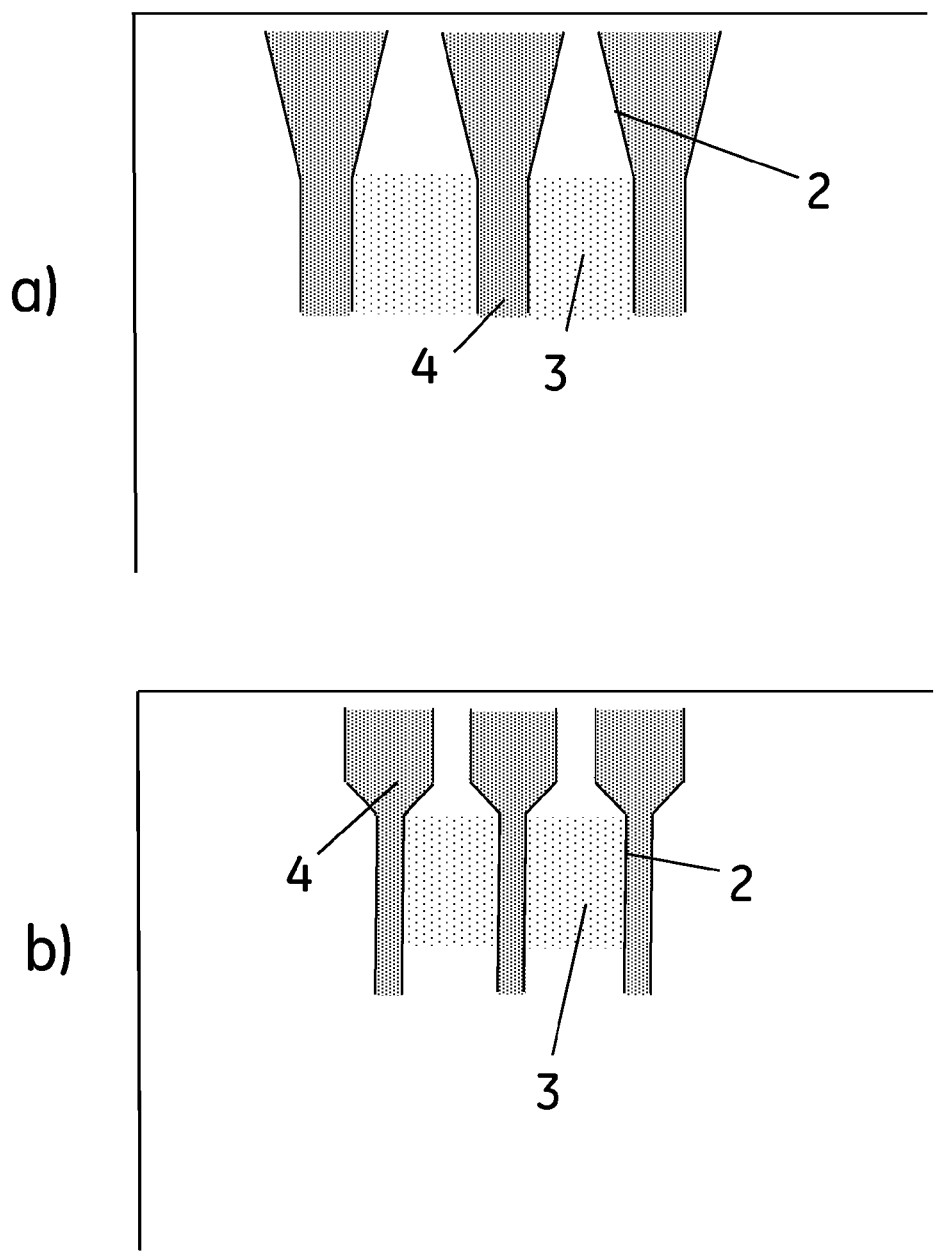
FIG. 4 shows alternative arrangements of the focusing barriers.

In one embodiment the focusing barriers are elongated in the running direction 5 of the electrophoresis gel assembly 1, as illustrated in FIG. 1. In a specific embodiment the focusing barriers extend at least along the length of the sample wells in the running direction. In one embodiment the focusing barriers extend forwards of the sample wells in the running direction, such as by up to 25% of the gel slab length in the running direction. In another embodiment the focusing barriers extend backwards of the sample wells relative to the running direction. More illustrations of focusing barriers 2 extending backwards of the sample wells 3 are given in FIG. 4. In FIG. 4 a) the focusing barriers 2 extend backwards of the sample wells 3 and in FIG. 4 b) they extend both backwards and forwards of the sample wells 3. As illustrated in FIG. 4, the part of the focusing buffer wells extending backwards of the sample wells can be wider than the part along the sample wells. An advantage of this is that a larger amount of focusing buffer can be applied without increasing the lateral distance between the sample wells.

Figure 5:
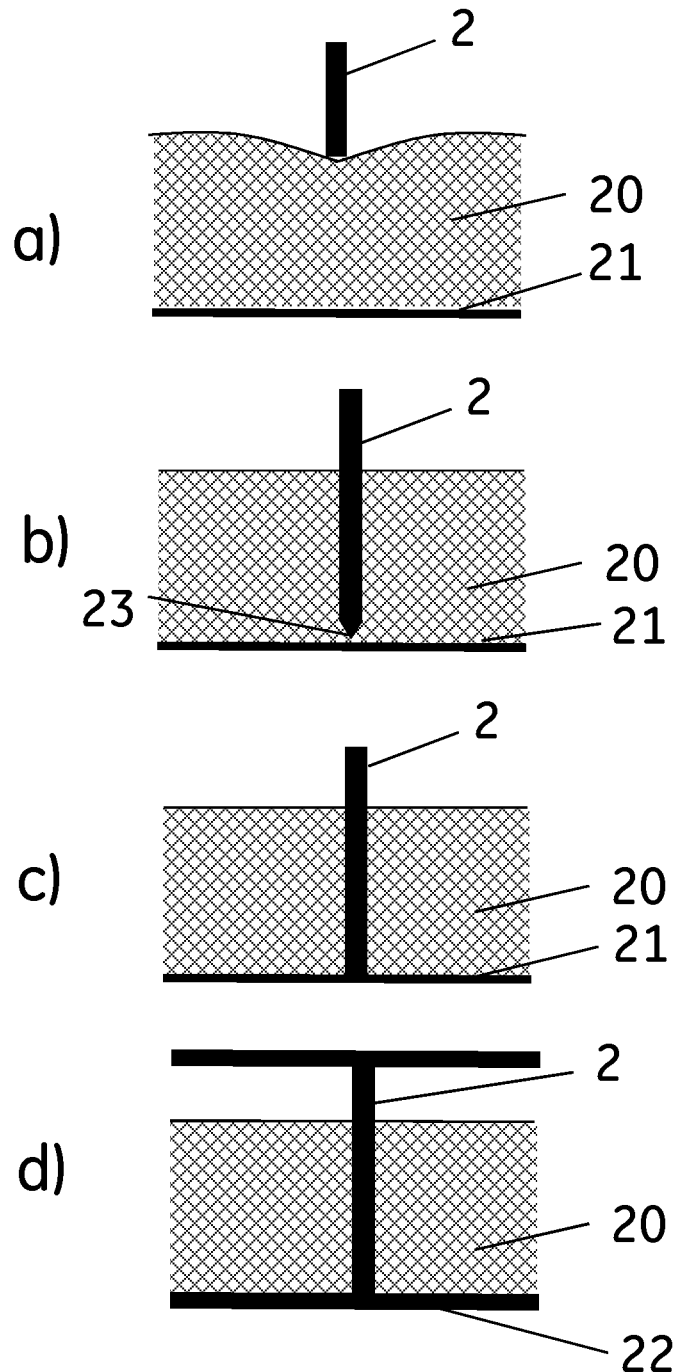
FIG. 5 shows alternative arrangements of the focusing barriers in relation to the gel slab.

In one embodiment the focusing barriers 2 are attached to the gel slab 20 by at least one clamp (not shown). The clamp can be one of many structures well known in the art, such as a spring device, a wedge device or a screw device. In a specific embodiment (illustrated in FIG. 5 a)) the gel slab 20 is compressed with at least 5% by the focusing barriers. The gel slab compression can be a result of the clamping and has the advantage of providing sealing between the barrier and the gel slab surface.

In one embodiment (illustrated by FIG. 5 b)) the focusing barriers 2 are cast or pressed into the gel slab 20. This can be accomplished by placing the focusing barriers in the mold and casting the gel slab with the barriers in place, or alternatively by pressing the barriers into the gel slab after casting. To facilitate pressing, the barriers can have a sharp edge 23 on the side facing the gel slab. Advantages of having the barriers penetrating into the gel slab, either through casting or pressing, are an efficient sealing and that a highly effective barrier against lateral ion transport through the gel slab is obtained.

In one embodiment (illustrated by FIG. 5 c) and d)) the focusing barriers 2 form an integral part of a gel support 21 or a cassette 22 which can be used for casting of a gel. This has the advantages of simplifying the casting process, providing good sealing and providing a highly effective barrier against lateral ion transport through the gel slab.

Figure 3:
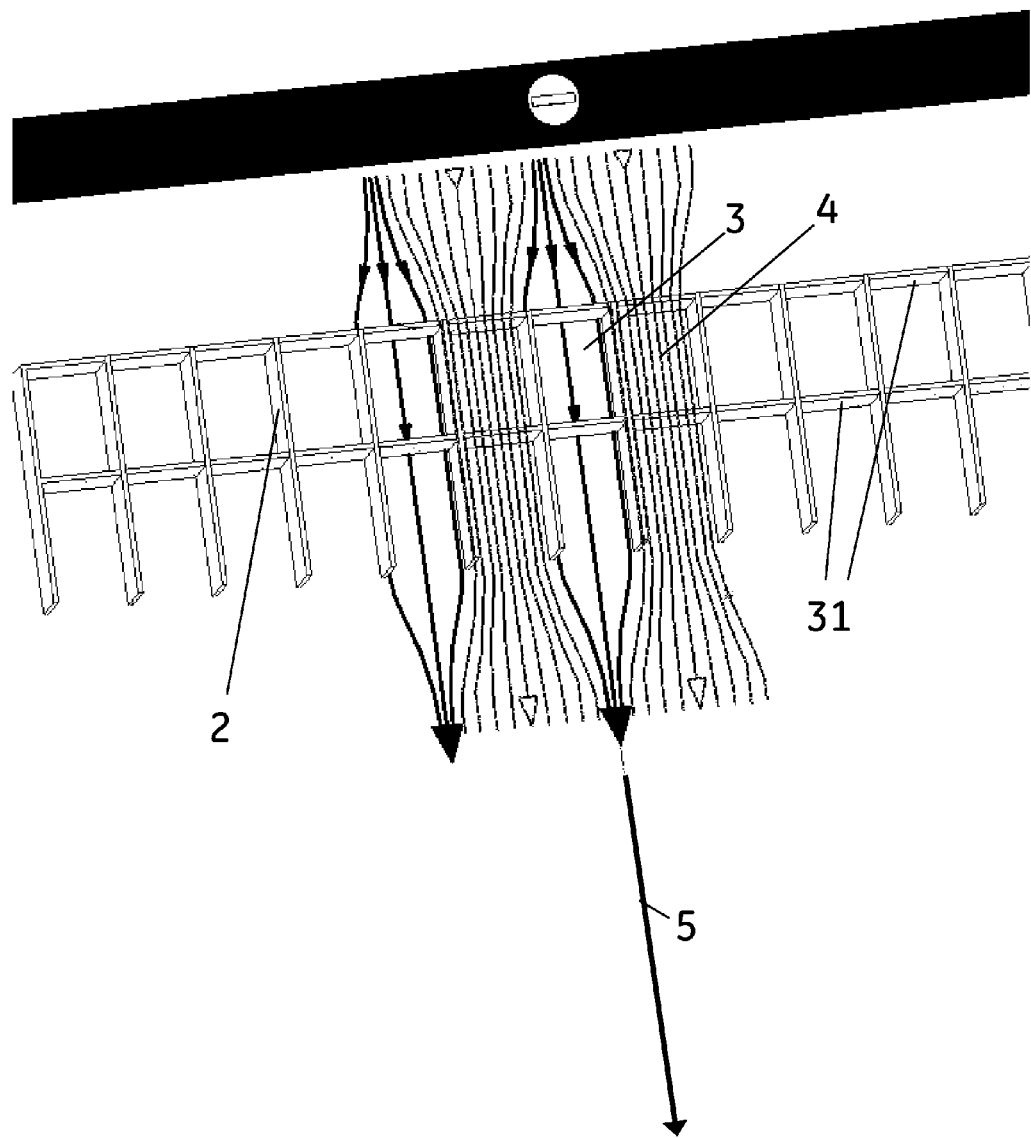
FIG. 3 shows an electrophoresis gel assembly with focusing barriers and support structures.

In one embodiment (illustrated in FIG. 3) the focusing barriers 2 are joined together by support structures 31. The support structures can e.g. be beams elongated in a direction orthogonal to the running direction 5. An advantage of having support structures is that several barriers can be handled simultaneously during e.g. clamping or casting operations. In one embodiment the support structures do not penetrate into the gel slab.

Figure 6:
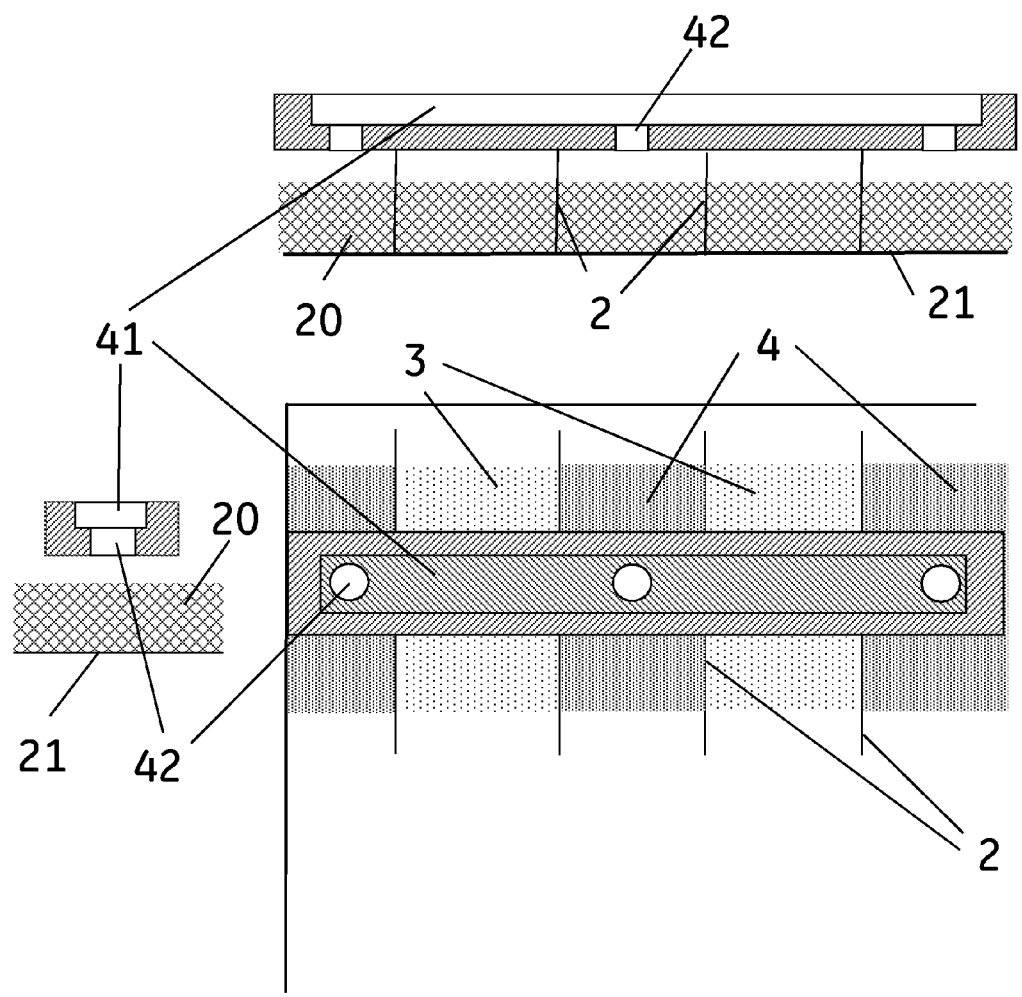
FIG. 6 shows a focusing buffer channel.

In one embodiment (illustrated in FIG. 6) at least two focusing buffer wells 4 are connected to each other by a focusing buffer channel 41. The focusing buffer channel can be arranged to allow the introduction of focusing buffer from at least one inlet point to at least two buffer outlet points 42. The buffer outlet points can be placed adjacent to at least two focusing buffer wells 4, such as with each buffer outlet point 42 adjacent to one focusing buffer well 4. The electrophoresis gel assembly may comprise several focusing buffer channels and it may also comprise at least one focusing buffer inlet well or inlet cup (not shown), connected to the focusing buffer channel(s). An advantage of having focusing buffer channels is that focusing buffer will only have to be added at one or a few inlet points instead of to each focusing buffer well separately.

On embodiment of the invention is a method for electrophoretic separation of biomolecules using an electrophoresis gel assembly as described above comprising a) supplying to at least one sample well 3 a biomolecule sample, b) supplying to at least two focusing buffer wells 4 adjacent to said sample well a focusing buffer having at least 25%, 100%, 200% or 600% higher conductivity than said biomolecule sample in said sample well and c) applying a voltage over the electrophoresis gel assembly. The sample may contain a sample buffer. In one embodiment the focusing buffer has at least 25%, 100%, 200% or 600% higher conductivity than the gel buffer or stacking gel buffer.

In one embodiment the separation method is performed at least one week after casting of the gel slab. Precast gels offer convenience for the user and the gels of the invention lend themselves well to use as precast gels, where the gel can be cast at one site, packaged, stored in a warehouse, transported to the user and used for separation up to three to six months after casting.

In one embodiment the biomolecules are proteins or nucleic acids. Typical protein samples can be derived from biological fluids (blood plasma, serum, urine, cerebrospinal fluid etc), tissues (animal tissue, plant tissue etc.), or cell cultures (microbial cells, animal cells, plant cells etc.) and nucleic acids like DNA or RNA can be derived from similar sources.

In one embodiment the separation is performed in the presence of a denaturing agent. The denaturing agent can be a surfactant, e.g sodium dodecyl sulfate (SDS) or a chaotrope, e.g. urea or guanidinium chloride. In one embodiment the separation is performed in the presence of a reducing agent, such as a thiol, e.g. mercaptoethanol, dithiothreitol (DTT) or dithioerythritol (DTE).

In one embodiment at least one biomolecule is labeled with a fluorescent or chemiluminescent reagent. Examples of fluorescent labeling reagents are Cy®dyes (GE Healthcare, Sweden) and other reactive dyes that can be covalently attached to proteins and nucleic acids.

In one embodiment the separated biomolecules are transferred to a porous substrate for detection. This can be a part of blotting methods like the Western blotting immunodetection of proteins or the Southern blotting hybridization detection of nucleic acids.

In one embodiment at least 10 biomolecule samples are separated in individual lanes on the gel.

On embodiment of the invention is a gel cassette for casting of a gel slab, comprising at least four focusing barriers. The cassette may comprise a compartment for the gel slab and compartments intended to form at least one sample well and at least two focusing buffer wells. The cassette can be manufactured from e.g. plastics, e.g. by injection molding.

One embodiment of the invention is focusing barriers to be arranged in an electrophoresis gel assembly comprising at least four focusing barriers. The focusing barriers may be individual or joined together by support structures.

Other features and advantages of the invention will be apparent from the following examples and from the claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

The invention claimed is:

1. An electrophoresis gel assembly comprising a gel slab, at least one sample buffer well, at least two focusing buffer wells adjacent to said sample buffer well, focusing barriers arranged between the at least two focusing buffer wells and the at least one sample well, wherein the at least one sample well is at least partially filled with a sample buffer, and wherein the focusing buffer wells are at least partially filled with a focusing buffer having a higher conductivity than the sample buffer, and wherein the at least two focusing buffer wells are connected to each other by a focusing buffer channel.

2. The electrophoresis gel assembly of claim 1, wherein the focusing barriers are elongated in the running direction.

3. The electrophoresis gel assembly of claim 1, wherein the focusing barriers extend at least along the length of the sample wells in the running direction.

4. The electrophoresis gel assembly of claim 1, wherein the focusing barriers extend forwards of the sample wells in the running direction and/or backwards of the sample wells relative to the running direction.

5. The electrophoresis gel assembly of claim 4, wherein the focusing barriers extend forwards of the sample wells in the running direction by up to 25% of the gel slab length in the running direction.

6. The electrophoresis gel assembly of claim 1, wherein the focusing barriers are attached to the gel slab by at least one clamp.

7. The electrophoresis gel assembly of claim 1, wherein the gel slab is compressed by at least 5% by the focusing barriers.

8. The electrophoresis gel assembly of claim 1, wherein the focusing barriers are cast or pressed into the gel slab.

9. The electrophoresis gel assembly of claim 1, wherein the focusing barriers form an integral part of a gel support or a cassette.

10. The electrophoresis gel assembly of claim 1, wherein the focusing barriers are joined together by support structures.

11. A method for electrophoretic separation of biomolecules using the electrophoresis gel assembly of claim 1 comprising:
    a) supplying to at least one sample well the buffer comprising a biomolecule sample;
    b) supplying to at least two focusing buffer wells adjacent to said sample well the focusing buffer; and
    c) applying a voltage over the electrophoresis gel assembly.

12. The method of claim 11, wherein the separation is performed at least one week after casting of the gel slab.

13. The method of claim 11, wherein the biomolecules are proteins or nucleic acids.

14. The method of claim 11, wherein the separation is performed in the presence of a denaturing agent.

15. The method of claim 11, wherein at least one biomolecule is labeled with a fluorescent or chemiluminescent reagent.

16. The method of claim 11, wherein the separated biomolecules are transferred to a porous substrate for detection.

17. The method of claim 11, wherein at least ten-biomolecule samples are separated in individual lanes on the gel.

18. The method of claim 11, wherein the focusing buffer has at least 25% higher conductivity than the buffer comprising a biomolecule.

19. The method of claim 11, wherein the focusing buffer has at least 100% higher conductivity than the buffer comprising a biomolecule.

20. The method of claim 11, wherein the focusing buffer has at least 200% higher conductivity than the buffer comprising a biomolecule.

21. The method of claim 11, wherein the focusing buffer has at least 600% higher conductivity than the buffer comprising a biomolecule.

* * * * *